United States Patent [19]
Yamamoto et al.

[11] Patent Number: 6,100,430
[45] Date of Patent: Aug. 8, 2000

[54] ALICYCLIC POLYAMINES AND PROCESS FOR THE PREPARATION THEREOF

[75] Inventors: Kenichi Yamamoto, Himeji; Kazuyuki Matsuoka, Nara; Hiroshi Yagihara, Himeji, all of Japan

[73] Assignee: Daicel Chemical Industries, Ltd., Osaka, Japan

[21] Appl. No.: 09/142,624

[22] PCT Filed: Jan. 20, 1998

[86] PCT No.: PCT/JP98/00192

§ 371 Date: Sep. 10, 1998

§ 102(e) Date: Sep. 10, 1998

[87] PCT Pub. No.: WO98/32729

PCT Pub. Date: Jul. 30, 1998

[30] Foreign Application Priority Data

Jan. 24, 1997 [JP] Japan ................................ 9-011065

[51] Int. Cl.⁷ ................. C07C 209/26; C07C 211/36; C07C 211/40
[52] U.S. Cl. ............. 564/455; 564/396; 564/398; 564/399; 564/431; 564/434; 564/443; 564/446; 564/461
[58] Field of Search ................... 564/396, 398, 564/399, 431, 434, 446, 455, 461, 443

[56] References Cited

U.S. PATENT DOCUMENTS 3,352,913 11/1967 Schmitt et al. .................. 564/455
4,925,974 5/1990 Gras .......................... 560/336

FOREIGN PATENT DOCUMENTS 1-160950 6/1989 Japan .

OTHER PUBLICATIONS

Poth et al., Chem Abst. 103:23851, 1985.
Hahn et al., Chem Abst. 102:96206, 1985.

*Primary Examiner*—Peter O'Sullivan
*Attorney, Agent, or Firm*—Birch, Stewart, Kolasch & Birch, LLP

[57] ABSTRACT

An alicyclic polyamine of the formula (1)

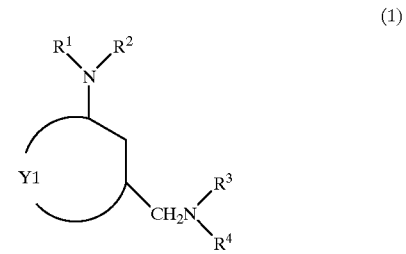

(1)

wherein $Y_1$ represents a saturated aliphatic hydrocarbon group and $R_1$ through $R_4$ are the same or different and each represents hydrogen atom, an alkyl group, a cycloalkyl group, an aryl group, or an aralkyl group. The alicyclic polyamine can be obtained by subjecting a 3-formylcycloalkanone or 3-formylcycloalkenone to reductive amination reaction.

11 Claims, No Drawings

ALICYCLIC POLYAMINES AND PROCESS FOR THE PREPARATION THEREOF

This application is the national phase under 35 U.S.C. §371 of prior PCT International Application No. PCT/JP98/00192 which has an International filing date of Jan. 20, 1998 which designated the United States of America, the entire contents of which are hereby incorporated by reference.

TECHNICAL FIELD

The present invention relates to an alicyclic polyamine which is useful as, for example, the diamine component of thermoplastic and thermosetting polymers and to a process for producing-the same.

BACKGROUND TECHNOLOGY

With the expanding application of polyurethane, polyamide, polyimide, and epoxy resin in recent years, there exists a demand for improvements in various polymer properties including weather resistance, water resistance, heat resistance, resistance to chemicals, electrical characteristics, and mechanical characteristics. In order to improve those polymer properties, several compounds, which are rather complicated in molecular structure, have been proposed for use as the diamine component of polymers. Among them are isophoronediamine, 4,4'-diamino-3,3'-diethyldiphenylmethane, diaminodiphenyl ether, 1,4-diaminobutane, and tolylenediamine, and so forth.

However, because of their complicated molecular structures, those diamines cannot be easily synthesized with high efficiency and at low cost on a commercial scale. Moreover, because the toxic prussic acid is generally used as an auxiliary starting material, their production on a commercial scale involves difficulties.

Meanwhile, as the curing agent for epoxy resin, there are known aliphatic polyamines such as diethylenetriamine, triethylenetetramine, diethylaminopropylamine, etc.; alicyclic polyamines such as isophoronediamine,etc.; and aromatic polyamines such as xylenediamine, diaminodiphenylsulfone,etc.; and so forth.

However, with those polyamines, all the above-mentioned polymer properties can hardly be implemented in a well-assorted balance.

It is, therefore, an object of the present invention to provide a polyamine useful as the diamine component of polymers and a process for producing the polyamine.

It is another object to provide a technology for providing the polyamine efficiently and a low cost.

DISCLOSURE OF INVENTION

Having explored into the art for accomplishing the above objects, the inventors of the present invention found that alicyclic polyamines having a certain defined structure are useful as the diamine component of various polymers and have perfected the present invention.

Thus, an alicyclic polyamine of the present invention is a compound of the following general formula(1).

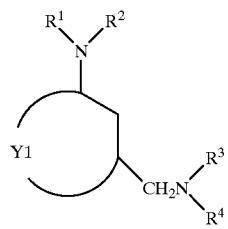

(1)

wherein $Y_1$ represents a saturated aliphatic hydrocarbon group; $R^1$ through $R^4$ may be the same or different and each represents hydrogen, an alkyl group, a cycloalkyl group, an aryl group, or an aralkyl group. This aliphatic polyamine can be produced by reductive amination of a 3-formylcycloalkanone or 3-formylcycloalkenone.

As used in this specification, the term "alicyclic polyamine" means an alicyclic compound containing two or more similar or dissimilar primary, secondary, and/or tertiary amino groups.

BEST MODE FOR CARRYING OUT THE INVENTION

Alicyclic Polyamine

Referring to any alicyclic polyamine of the above formula (1), the bivalent saturated aliphatic hydrocarbon group designated by $Y_1$ may be straight-chain or branched, and, in the case of a branched-chain hydrocarbon group, the same carbon atom may be substituted by 1 or 2 alkyl groups. The aliphatic hydrocarbon group includes, for example, $C_{1-10}$ alkylene groups such as methylene, ethylene, propylene, trimethylene, 2-methyltrimethylene, 2,2-dimethyltrimethylene, tetramethylene, 2-methyltetramethylene, 2,2-dimethyltetramethylene, pentamethylene, hexamethylene, and so forth. Preferred straight-chain and branched alkylene groups are $C_{2-8}$ alkylene groups, with $C_{2-6}$ alkylene groups being particularly preferred.

Those aliphatic hydrocarbon groups may each be substituted, in suitable positions, by various substituent groups, for example, amino, hydroxy, $C_{1-4}$ alkoxy, carboxy, alkoxycarbonyl, alicyclic hydrocarbon groups (cycloalkyl, cycloalkenyl, cycloalkinyl, etc.), and/or aromatic hydrocarbon groups (aryl groups such as phenyl).

Referring, further, to the above formula (1), $R^1$ through $R^4$ are the same or different and each represents hydrogen atom, alkyl, cycloalkyl, aryl, or aralkyl groups. The alkyl groups includes, for example, straight-chain or branched $C_{1-10}$ alkyl groups such as methyl, ethyl, propyl, isopropyl, butyl, t-butyl, pentyl, hexyl, octyl, and so forth. The preferred alkyl groups are $C_{1-6}$ alkyl, and particularly $C_{1-4}$ alkyl. The cycloalkyl includes but is not limited to $C_{3-10}$ cycloalkyl groups such as cyclopropyl, cyclobutyl, cyclopentyl, cyclohexyl, and so forth. The aryl includes but is not limited to phenyl and naphthyl. The aralkyl includes but is not limited to $C_{7-10}$ aralkyl groups such as benzyl and phenethyl. Those alicyclic polyamines can be selectively used according to the intended application.

The preferred alicyclic polyamines are those alicyclic polyamines in which $R^1$ to $R^4$ represent hydrogen atom or a lower($C_{1-4}$)alkyl group (such as 3-N-methylaminomethyl-N-methylcyclohexylamine, 3-N-ethylaminomethyl-N-ethylcyclohexylamine, 3-N,N-dimethylaminomethyl-N,N- dimethylcyclohexylamine, 3-N,N-diethylaminomethyl-N, N-diethylcyclohexylamine, etc.). Particularly, 3-aminomethylcycloalkylamines wherein $R^1$ to $R^4$ invariably represent hydrogen atom are useful as starting materials for the production of polymers, among other uses.

The 3-aminomethylcycloalkylamine mentioned above includes, for example, to 3-aminomethylcyclopentylamine, 3-aminomethylcyclohexylamine, 3-aminomethyl-5-methylcyclohexylamine, 3-aminomethylcycloheptylamine, 3-aminomethyl-5,5-dimethylcyclohexylamine, 3-aminomethylcyclooctylamine, 3-aminomethyl-5-methylcyclooctylamine, and 5-phenyl-3-aminomethylcyclohexylamine, and so forth. The preferred 3-aminomethylcycloalkylamine is 3-aminomethyl-5,5-dimethylcyclohexylamine.

The alicyclic polyamine can not only be used as it is but also may be used in the form of a salt prepared by reacting it with an acid.

When such an alicyclic polyamine is used as a starting material in the production of polymers (e.g. the diamine component of a polyamide or a polyimide, a starting material for a polyisocyanate compound or epoxy resin, or a curing agent or modifier for epoxy resin), polymers with excellent weather resistance, inhibition the decrease of mechanical strength, and good resistance to chemicals can be obtained due to the existence of an optionally substituted amino group on the alicyclic nucleus and an optionally substituted amino group on the side-chain methyl group. Moreover, because a cyclic structure is introduced, polymers with high melting points and improved heat resistance can be obtained. In addition, because of its alicyclic structure, polymers of low polarity, good water resistance, and excellent electrical characteristics can be obtained.

The alicyclic secondary amines and alicyclic tertiary amines can also be used as catalysts, for instance.

Process for Producing an Alicyclic Polyamine

As illustrated in the following reaction process scheme, the process of the present invention comprises subjecting a 3-formylcycloalkanone or 3-formylcycloalkenone of the following formula (2) (hereinafter may referred to briefly as the substrate compound) to reductive amination in the presence of a catalyst to give an alicyclic diamine of the following formula (1). The substrate 3-formylcycloalkanone or 3-formylcycloalkenone of the formula (2) can be obtained by various methods, for example by oxidizing a 3-methylcycloalkanone or 3-methylcycloalkenone of the following formula (3).

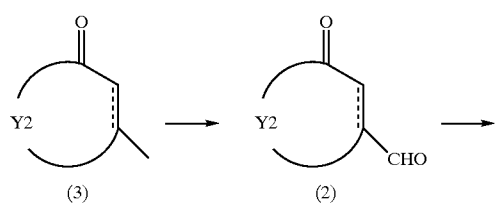

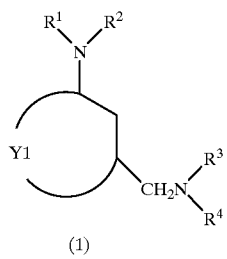

wherein $Y_1$ represents a saturated aliphatic hydrocarbon group; $Y_2$ represents a saturated or unsaturated hydrocarbon group; $R^1$ to $R^4$ are the same or different and each represents hydrogen atom, an alkyl group, a cycloalkyl group, an aryl group, or an aralkyl group.

Process for Producing Compound (2)

The substrate compound of the above formula (2) - (3-formylcycloalkanone or 3-formylcycloalkenone) can be produced by a process which comprises oxidizing a 3-methylcycloalkanone or 3-methylcycloalkenone of the above formula (3) with oxygen in the presence of a catalyst such as a metal oxide (selenium oxide, chromium oxide, dichromic acid, and oxides of copper, silver, lead, etc.), a naphthenic acid salt (cobalt, chromium, or other salt), or a vanadium oxide catalyst ($V_2O_5$—$SnO_2$, $V_2O_5$-$SnO_2$—$Fe_2O_3$, $V_2O_5$—$Fe_2O_3$, etc.), a process which, as described in Japanese Patent Application Laid-open No. 154528/1983 (JP-A-58-154528), comprises oxidizing the substrate compound with oxygen in the presence of at least one metal salt selected from the group consisting of salts of iron, ruthenium, rhodium, cobalt, etc., or an oxidation process using a heteropolyacid or a salt thereof as the catalyst. Preferred is the process for producing a 3-formylcycloalkenone by using a 3-methylcycloalkenone in combination with, as the oxidation catalyst, a heteropolyacid or a salt thereof.

The heteropolyacid is an oxy-acid condensate containing 2 or more dissimilar center ions and is also known as a heteronuclear condensed acid. The heteropolyacid may for example be composed of the oxy-acid ion (e.g. phosphate, silicate, etc.) of an element such as P, As, Sn, Si, Ti, or Zr and the oxy-acid (e.g. vanadic acid, molybdic acid, tungstic acid, etc.) of an element such as V, Mo, or W. A variety of heteropolyacids for use as catalysts can be obtained according to various combinations of such oxy-acid ion and oxy-acid.

The preferred heteropolyacid anion can be expressed by $XM_{12}O_{40}$. "X" represents an element such as Si, P, or the like and "M" represents an element such as Mo, W, V, or the like. The heteropolyacid having such a composition includes phosphomolybdic acid, phosphotungstic acid, silicomolybdic acid, silicotungstic acid, phosphovanadomolybdic acid, and so forth. The preferred heteropolyacid are phosphomolybdic acid and phosphovanadomolybdic acid, with phosphovanadomolybdic acid being particularly preferred.

Phosphovanadomolybdic acid or its salt is expressed by the following formula.

$$A_{3+n}[PV_nMo_{12-n}O_4]$$

wherein "A" represents a heteropolyacid cation and n represents an integer of 1 to 10.

The heteropolyacid cation designated by "A" need not only be hydrogen atom but also may be a cation other than H, for example $NH_4$, an alkali metal (e.g. Cs, Rb, K, Na, Li) cation or an alkaline earth metal (e.g. Ba, Sr, Ca, Mg) cation.

While the heteropolyacid as a free heteropolyacid is sufficiently active, at least some of the hydrogen cation atoms as counter cation of the heteropolyacid may be replaced with a different cation. By such partial substitution of the heteropolyacid, the heteropolyacid can be insolubilized to enhance its stability and heat resistance, thus providing the more useful catalyst. The species of substituent cation that can be used is not particularly restricted but includes $NH_4$, alkali metals (Cs, Rb, K, Na, Li, etc.) cation and alkaline earth metals (e.g. Ba, Sr, Ca, Mg) cation, and so forth. Particularly when the heteropolyacid is partially substituted by ammonium cations to make a mixed cation composition of H and $NH_4$, the catalyst activity and stability are still more improved. In this connection, the molar ratio of $NH_4$ to H may be $NH_4/H$=about 0.1 to 10, preferably $NH_4/H$=about 0.2 to 8, and more preferably $NH_4/H$=about 0.3 to 5.

The value of "n" can be judiciously selected in consideration of oxidizing ability and stability, and may for example be about 1 to 10, preferably about 4 to 10 (for example 4 to 8), and more preferably about 5 to 8. When the counter cation moiety of the heteropolyacid is constituted by H and a cation other than H (for example $NH_4$), the value of "n" may be about 4 to 10 in many instances. Such heteropolyacids inclusive of their salts can be used each alone or in combination.

The heteropolyacid inclusive of its salt can be used as it is as a catalyst but may be used in the form of a supported catalyst or solid catalyst as immobilized on a suitable supports. The catalyst activity of the heteropolyacid is increased when it is so immobilized.

The support or carrier which can be used for immobilizing the catalyst substance includes the conventional support or carrier materials inclusive of inorganic supports such as activated carbon, alumina, silica, silicon carbide, silica-alumina, bentonite, magnesia, titania, vanadia, zirconia, zeolite, diatomaceous earth, kaolin, etc. and organic supports such as styrene-divinylbenzene copolymer. The preferred support includes porous supports such as activated carbon, alumina, titania, silicon carbide, silica-alumina, bentonite, and zeolite, and so on. Particularly preferred is activated carbon. When activated carbon is used, the selectivity for oxidation of the 3-methyl group of the substrate compound can be still more improved. Activated carbon may be particulate or fibrous.

The specific surface area of the support is not particularly restricted but may for example be about 10 to 4500 $m^2/g$, preferably about 50 to 4000 $m^2/g$, and usually about 100 to 3000 $m^2/g$. For enhanced catalyst activity, the preferred specific surface area of activated carbon may for example be about 300 to 4000 $m^2/g$, preferably about 400 to 3000 $m^2/g$. In many instances, activated carbon with a specific surface area of about 500 to 2000 $m^2/g$ is selected.

The mean pore diameter of activated carbon may be about 5 to 200 Angstrom units, preferably about 10 to 100 Angstrom units. The pore volume of activated carbon may for example be about 0.1 to 10 ml/g, preferably about 0.3 to 5 ml/g.

The amount of the heteropolyacid inclusive of its salt relative to the support can be freely selected within the range not detracting from catalyst activity and, based on 100 parts by weight of the support, may for example be about 0.1 to 100 parts by weight, preferably about 0.5 to 50 parts by weight, more preferably about 5 to 30 parts by weight, and, for still better results, about 5 to 20 parts by weight.

Immobilization of the heteropolyacid inclusive of its salt on such a support can be effected by the conventional technology, for example immersion, coating, spray-coating, adsorption, or precipitation. Particularly, a procedure capable of supporting the catalyst component uniformly in a highly dispersed state on the support, for example an immersion process or an adsorption process, can be used with advantage.

In immobilizing the heteropolyacid or its salt, it is common practice to use a solvent such as water and cause a solution of the catalyst component in such a solvent to be uniformly supported.

The amount of the heteropolyacid or its salt is dependent on its species but is usually selected from the range of 0.1 to 50 weight % in terms of the heteropolyacid or salt relative to compound (3).

In the practice of the present invention, not only oxygen or an oxygen-containing gas but also compounds capable of liberating oxygen can be used as the oxygen source. The oxygen source may for example be oxygen gas of high purity. Where necessary, the oxygen gas may be diluted with an inert gas such as nitrogen, helium, argon, or carbon dioxide gas, and the diluted oxygen gas may be fed to the reaction system, When an inert gas is used as a diluent gas, it is possible to use air in lieu of oxygen so that the nitrogen in the air may serve as the inert gas.

The concentration of oxygen per mole of the substrate compound may be 0.5 mole or more (0.5 to 1000 moles), preferably a stoichiometric excess (1 to 1000 moles). The reaction is usually carried out in the presence of a large excess of oxygen, for example in an oxygen atmosphere or an oxygen-containing gas atmosphere.

The oxidation reaction may be whichever of gas-phase oxidation and liquid-phase oxidation. The reaction can be conducted in the absence of a solvent or in the presence of an inert solvent indifferent to the reaction. The solvent mentioned just above includes aromatic hydrocarbons such as benzene, toluene, xylene, ethylbenzene, etc.; aliphatic hydrocarbons such as hexane, heptane, octane, etc.; alicyclic hydrocarbons such as cyclohexane etc.; halogenated hydrocarbons such as carbon tetrachloride, chloroform, dichloromethane, 1,2-dichloroethane, etc.; carboxylic acids such as acetic acid, propionic acid, butyric acid, etc.; ketones such as acetone, methyl ethyl ketone, etc.; esters such as methyl acetate, ethyl acetate, isopropyl acetate, butyl acetate, etc.; ethers such as diethyl ether, dibutyl ether, dimethoxyethane, dioxane, tetrahydrofuran, diethylene glycol dimethyl ether, 1-methoxy-2-propanol, etc.; amides such as N,N-dimethylformamide, N,N-dimethylacetamide, etc.; and nitriles such as acetonitrile, propionitrile, benzonitrile, and so forth. Those solvents can be used each alone or in combination.

The reaction temperature can be freely selected according to the desired reaction rate and selectivity and may for example be about 30 to 300° C., preferably about 50 to 200° C.

Substrate Compound

The 3-formylcycloalkanone or 3-formylcycloalkenone of the formula (2), which is used as the substrate compound, is a cyclic ketone having a formyl group in the β-position and includes 3-formylcycloalkanones such as 3-formylcyclopentanone, 3-formylcyclohexanone, 5-methyl-3-formylcyclohexanone, 3-formylcycloheptanone, 5,5-dimethyl-3-formylcyclohexanone, 3-formylcyclooctanone, 5-methyl-3-formylcyclooctanone, 5-phenyl-3-formylcyclohexanone, etc. and [ 3]-formylcycloalkenones such as 3-formylcyclopentenone, 3-formylcyclohexenone, 5-methyl-3-formylcyclohexenone, 3-formylcycloheptenone, 5,5-dimethyl-3-formylcyclohexenone, 3-formylcyclooctenone, 5-methyl-3-formylcyclooctenone, 5-phenyl-3-formylcyclohexenone, and so forth. Only provided that the above basic structural feature is retained, bicyclic fused compounds sharing two or more carbon atoms (for example 4-formylbicyclo[4.4.0]decan-3-en-2-one) may also be used.

Reductive Amination Reaction

The reductive amination reaction for converting a compound of the formula (2) to a compound of the formula (1) can be carried out using hydrogen and at least one member selected from the group consisting of ammonia, primary amines, and secondary amines in the presence of a catalyst.

The catalyst which can be used for this reductive amination reaction (hereinafter may referred to as catalyst component) includes metal catalysts such as nickel compounds (reducing nickel, Raney nickel, etc.), cobalt compounds (cobalt, Raney cobalt, etc.), platinum compounds (e.g. platinum black, platinum oxide, etc.), palladium compounds (e.g. palladium, palladium black, etc.), rhodium, ruthenium, cobalt-rhenium-molybdenum catalyst, copper chromite, copper-chromium catalyst, etc. The preferred catalysts are nickel compounds, cobalt compounds, platinum compounds, palladium compounds, and cobalt-rhenium-molybdenum catalyst.

The above catalyst can be used as it is but may be used as a supported catalyst or solid catalyst as immobilized on a support.

The support or carrier which can be used for supporting the above catalyst component includes the conventional support or carrier materials inclusive of inorganic supports such as activated carbon, carbon black, alumina, silica, silicon carbide, silica-alumina, bentonite, magnesia, titania, vanadia, zirconia, zeolite, diatomaceous earth, kaolin, barium sulfate, etc. and organic supports such as styrene-divinylbenzene copolymer. The preferred support includes porous supports such as activated carbon, alumina, carbon black, silicon carbide, silica-alumina, bentonite, zeolite, and barium sulfate.

The specific surface area of the support is not particularly restricted but may for example be about 0.01 to 4500 $m^2/g$, preferably about 0.1 to 4000 $m^2/g$, and usually about 0.2 to 3000 $m^2/g$.

The amount of the catalyst relative to the support can be selected within the range contributory to enhanced catalyst activity and may for example be about 0.05 to 100 parts by weight, preferably about 0.1 to 50 parts by weight, more preferably about 0.5 to 30 parts by weight, and, particularly, 1 to 20 parts by weight, based on 100 parts by weight of the support.

Immobilization of the catalyst on the support or carrier can be effected by the conventional technology, for example immersion, coating, spray-coating, adsorption, or precipitation. Particularly, a procedure capable of supporting the catalyst component uniformly in a highly dispersed state on the support, for example an immersion process or an adsorption process, can be used with advantage.

The amount of the catalyst depends on its species but is generally selected from the range of 1 to 50 weight %, as catalyst component, relative to the substrate compound.

The hydrogen source for use in the catalytic reduction reaction according to the present invention includes hydrogen and a hydrogen-containing gas. As such a hydrogen source, hydrogen gas of high purity can be used ,and, where necessary, hydrogen gas diluted with an inert gas indifferent to the reaction, such as nitrogen, helium, or argon gas, may be fed to the reaction system.

The hydrogen pressure is usually selected within the range of about 1 to 200 $kgf/cm^2$, preferably about 5 to 150 $kgf/cm^2$, and more preferably about 10 to 100 $kgf/cm^2$.

The ammonia or amine source which can be used for the amination reaction according to the present invention includes not only ammonia and ammonia-containing gases but also compounds capable of liberating ammonia (e.g. ammonium salts or ammmono-salt) and amines. The amines include primary amines (aliphatic primary amines such as methylamine, ethylamine, propylamine, isopropylamine, butylamine, pentylamine, hexylamine, heptylamine, etc.; alicyclic primary amines such as cyclopropylamine, cycloheptylamine, cyclohexylamine, etc.; aromatic primary amines such as aniline, benzylamine, etc.) and secondary amines (aliphatic secondary amines such as dimethylamine, diethylamine, dipropylamine, diisopropylamine, etc.; alicyclic secondary amines such as dicyclopropylamine, dicycloheptylamine, dicycohexylamine, etc.; aromatic secondary amines such as methylaniline, dibenzylamine, etc.). While the amine source may be gaseous, liquid, or solid according to the kind of amine, any of them can be used. When a gaseous amine source is used, it may be a highly purified gas or, where necessary, such a gas may be diluted with an inert gas indifferent to the reaction, such as nitrogen, helium, or argon gas. The gaseous amine may be fed to the reaction system. Such ammonia or amine sources can be used each alone or in combination according to the objective compound.

The proportion of the ammonia or amine may for example be 2 to 100 moles, preferably about 2 to 50 molar equivalents, relative to 1 mol of the 3-formylcycloalkenone used.

The reductive amination reaction can be carried out in the absence of a solvent or in an inert solvent. The solvent which can be used for this reductive amination reaction includes not only the same solvents as mentioned for the oxidation reaction (aliphatic hydrocarbons, alicyclic hydrocarbons, esters, amides, ethers, etc.) but also alcohols such as methanol, ethanol, propanol, isopropanol, butanol, ethyleneglycol, diethyleneglycol, and 1,4-butanediol, among others. The solvent which is usually employed includes alcohols and ethers. Those solvents can be used each alone or in combination.

The proportion of the solvent relative to 1 part by weight of 3-formylcycloalkanone or 3-formylcycloalkenone is about 1 to 100 parts by weight, preferably about 3 to 50 parts by weight, and more preferably about 5 to 30 parts by weight.

The reaction temperature can be judiciously selected with reference to reaction kinetics and selectivity and may for example be about 30 to 300° C., preferably about 50 to 250° C., and more preferably about 100 to 200° C.

This reaction can be carried out substantially in the same manner as the conventional reductive amination reaction. When a solvent is used, hydrogen is introduced into a reaction system comprising a 3-formylcycloalkanone or 3-formylcycloalkenone, at least one member selected from the group consisting of ammonia, primary amines and secondary amines, and a solvent in the presence of a hydrogenation catalyst. Particularly, the formation of byproducts is suppressed when the reaction is conducted by introducing hydrogen into a reaction system comprising a 3-formylcycloalkenone, at least one member selected from the group consisting of ammonia, primary amines and secondary amines, and a solvent in the presence of a hydrogenation catalyst.

The reaction product alicyclic polyamine can be easily isolated and purified by the conventional separation procedure such as filtration, concentration, distillation, extraction, crystallization, recrystallization, or column chromatography, or a combination of such procedures.

INDUSTRIAL APPLICABILITY

The resulting alicyclic polyamine of the present invention finds application as a reagent, an intermediate of drugs and perfumes, a compound for the production of polymers (e.g. polyamides, polyimides, epoxy resin, polyurethane, etc.), or an amine catalyst. Particularly, 3-aminomethylcycloalkylamines are of value as starting materials for the production of polymers.

The polyamide can be obtained by subjecting a diamine component at least including a 3-aminomethylcycloalkylamine, and a dicarboxylic acid component such as adipic acid to condensation reaction. The polyimide can be obtained by reacting a tetracarboxylic anhydride with a diamine component at least including a 3-aminomethylcycloalkylamine or reacting a bismaleimide with a diamine component at least including a 3-aminomethylcycloalkylamine. The epoxy resin can be obtained by reacting a diamine component at least including a 3-aminomethylcycloalkylamine with epichlorohydrin. A polyisocyanate for use as a starting material of polyurethane can be obtained by reacting a 3-aminomethylcycloalkylamine with phosgene.

The epoxy resin can be improved in mechanical strength and chemical resistance by adding a 3-aminomethylcycloalkylamine or an alicyclic polyamine comprising secondary or tertiary amino functions as a curing agent.

In accordance with the present invention, alicyclic polyamines useful as the diamine component of polymers can be provided. Moreover, such alicyclic polyamines can be produced with high efficiency.

EXAMPLES

The following examples illustrate the present invention in further detail, it being to be understood, however, that these examples should by no means be construed as defining the scope of the invention.

Example 1

To 43.90 g of sodium metavanadate and 49.32 g of sodium molybdate was added 300 ml of water and the mixture was heated at 95° C. to prepare a solution. To this solution, a solution prepared from 45.6 g of 85% phosphoric acid and 60 ml of water was added, and the mixture was kept at 95° C. for 1 hour, with constant stirring. The mixture was then cooled to 0° C. and a solution of 35.6 g of ammonium chloride in 126ml of water was added. Whereupon a brown precipitate separated out. The precipitate was collected by filtration and recrystallized twice from water to provide a heteropolyacid ammonium salt. Analysis of this heteropolyacid ammonium salt was $(NH_4)_5H_6[PV_8Mo_4O_{40}]9.6H_2O.$ To a solution prepared from 200 mg of the above heteropolyacid ammonium salt and 4000 ml of water was added 1800 mg of activated carbon, and the mixture was stirred for 1 hour and then allowed to stand at room temperature. It was then filtered and the cake was washed with 4000 ml of water and dried at 80° C. to provide a catalyst supported on the carbon.

A glass flask (capacity 50 ml) was charged with 1.75 g of the above catalyst, 1.38 g of isophorone, and 20 g of toluene and the reaction was carried out under oxygen atmosphere at the reflux temperature for 20 hours. Analysis of this reaction mixture by gas chromatography revealed that 93% of isophorone had reacted, with 62% of the reacted isophorone having been converted to 5,5-dimethyl-3-formylcyclohexanone (yield 58 weight t).

An autoclave (capacity 300 ml) equipped with an electromagnetic stirrer was charged with a solution prepared from 5 g of 5,5-dimethyl-3-formylcyclohexanone and 100 g of methanol, 1 g of Raney nickel, and 15 g of ammonia. After the temperature was increased to 120° C., the reaction was carried out under a hydrogen partial pressure of 50 kgf/cm$^2$ at a stirring speed of 800 to 1000 rpm for 2 hours.

After completion of the reaction, the autoclave was cooled and relieved of pressure and the reaction mixture was withdrawn. The catalyst was then filtered off and the methanol was evaporated off at atmospheric pressure, whereby 4.1 g of a substance was obtained. Of this substance, 3-aminomethyl-5,5-dimethylcyclohexylamine accounted for97.4%by weight. This substance was analyzed by mass spectrometry, elemental analysis and infrared absorptiometry.

Mass Spectrum

MS molecular ion peaks (m/e): 156 (theoretical molecular mass 156), 127, 126, 113, 70, 56, and 435.

Elemental analysis (for $C_9N_2H_2O$)

C N H

Found : 69.5; 12.7; 17.8
Calcd.: 69.2; 12.8; 17.9

Infrared Absorption Spectrum
Measured band: 3280 (cm$^{-1}$)

Example 2

A heteropolyacid ammonium salt of the composition $(NH_4)_3H_8[PV_8Mo_{40}O_{40}]$ was immobilized or supported on activated carbon as in Example 1. Using this catalyst-on-carbon, the reaction was carried out in the same manner as in Example 1. As a result, 94% of isophorone reacted and 60% of the reacted isophorone was converted to 5,5-dimethyl-3-formylcyclohexanone (yield 56 weight %).

This 5,5-dimethyl-3-formylcyclohexanone was subjected to the same reductive amination reaction as in Example 1 to provide 3-aminomethyl-5,5-dimethylcyclohexylamine as in Example 1.

Example 3

A heteropolyacid ammonium salt of the composition $(NH_4)_4H_4[PV_5Mo_7O_{40}]$ was immobilized or supported on activated carbon as in Example 1. Using this catalyst-on-carbon, the reaction was conducted in the same manner as in Example 1. As a result, 83% of isophorone reacted and 60% of the reacted isophorone was converted to 5,5-dimethyl-3-formylcyclohexanone (yieldw 50 weight %).

When this 5,5-dimethyl-3-formylcyclohexanone was subjected to reductive amination reaction in the same manner as in Example 1, 3-aminomethyl-5,5-dimethylcyclohexylamine was obtained as in Example 1.

Example 4

A heteropolyacid ammonium salt of the composition $(NH_4)_3H_4[PV_4Mo_8O_{40}]$ was immobilized or supported on activated carbon in the same manner as in Example 1. Using this catalyst-on-carbon, the reaction was carried out in the same manner as in Example 1. As a result, 79% of isophorone reacted and 61% of the reacted isophbrone was converted to 5,5-dimethyl-3-formylcyclohexanone (yield 48 weight %).

When the above 5,5-dimethyl-3-formylcyclohexanone was subjected to reductive amination as in Example 1, 3-aminomethyl-5,5-dimethylcyclohexylamine was obtained as in Example 1.

It will be apparent from the above examples, the novel 3-aminomethylcycloalkylamine can thus be obtained. Moreover, by the process of the present invention, 3-aminomethylcycloalkylamines can be produced with high conversion and high selectivity.

What is claimed is:

1. An alicyclic polyamine of the following formula

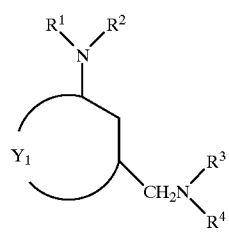

(1)

wherein $Y_1$ represents a saturated aliphatic hydrocarbon group comprising a carbon atom which is substituted by 2 alkyl groups,
$R^1$ and $R^4$ are the same or different and each represents hydrogen atom, an alkyl group, a cycloalkyl group, and aryl group, or an aralkyl group.

2. The alicyclic polyamine according to claim 1, wherein $Y_1$ is a $C_{1-10}$ alkylene group and $R_1$ through $R_4$ are the same or different and each represents hydrogen atom or a $C_{1-4}$ alkyl group.

3. The alicyclic polyamine according to claim 1, which is a 3-aminomethylcycloalkylamine.

4. The alicyclic polyamine according to claim 1, which is 3-aminomethyl-5,5-dimethylcyclohexylamine.

5. The alicyclic polyamine according to claim 1, wherein the aliphatic hydrocarbon group may be substituted by a substituent selected from the group consisting of amino, hydroxy, $C_{1-4}$alkoxy, carboxy, alkoxycarbonyl, alicyclic hydrocarbon groups and aromatic hydrocarbon groups.

6. The alicyclic polyamine according to claim 1, wherein the cycloalkyl group is selected from the group consisting of cyclopropyl, cyclobutyl, cyclopentyl and cyclohexyl.

7. The alicyclic polyamine according to claim 1, wherein the aryl group is selected from the group consisting of phenyl and naphthyl.

8. The alicyclic polyamine according to claim 1, wherein the aralkyl group is selected from the group consisting of benzyl and phenethyl.

9. A process for producing an alicyclic polyamine of the following formula

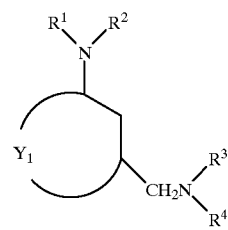

(1)

wherein $Y_1$ represents a saturated aliphatic hydrocarbon group and $R^1$ through $R^4$ are the same or different and each represents hydrogen atom, an alkyl group, a cycloalkyl group, an aryl group, or an aralkyl group, which comprises subjecting a 3-formylcycloalkanone or 3-formylcycloalkenone of the following formula (2) to reductive amination reaction:

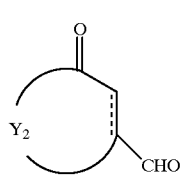

(2)

wherein $Y_2$ represents a saturated or unsaturated aliphatic hydrocarbon group.

10. The process according to claim 9, which comprises oxidizing a 3-methylcycloalkanone or 3-methylcycloalkenone and subjecting the resulting 3-formylcycloalkanone or 3-formylcycloalkenone of formula (2) to reductive amination reaction.

11. The process according to claim 9, wherein said reductive amination reaction is conducted by introducing hydrogen into a reaction system comprising said 3-formylcycloalkanone or 3-formylcycloalkenone, at least one member selected from the group consisting of ammonia, primary amines, and secondary amines, and a solvent in the presence of a hydrogenation catalyst.

* * * * *